United States Patent
Kesling

(10) Patent No.: US 6,834,761 B1
(45) Date of Patent: Dec. 28, 2004

(54) PACKAGE FOR READY MOUNTABLE BONDABLE ORTHODONTIC APPLIANCES AND METHOD OF MAKING SAME

(75) Inventor: Andrew C. Kesling, LaPorte, IN (US)

(73) Assignee: TP Orthodontics, Inc., Westville, IN (US)

( * ) Notice: Subject to any disclaimer, the term of this patent is extended or adjusted under 35 U.S.C. 154(b) by 219 days.

(21) Appl. No.: 10/321,347

(22) Filed: Dec. 17, 2002

(51) Int. Cl.$^7$ ............................................. A61B 19/02
(52) U.S. Cl. ........................ 206/63.5; 206/813; 53/403
(58) Field of Search .................. 206/63.5, 438, 206/369, 368, 493, 813; 53/403, 408, 425

(56) References Cited

U.S. PATENT DOCUMENTS

| | | | |
|---|---|---|---|
| 4,978,007 A | 12/1990 | Jacobs et al. | |
| 5,172,809 A | 12/1992 | Jacobs et al. | |
| 5,328,363 A | 7/1994 | Chester et al. | |
| 5,348,154 A | 9/1994 | Jacobs et al. | |
| 5,350,059 A | 9/1994 | Chester et al. | |
| 5,538,129 A | 7/1996 | Chester et al. | |
| 5,636,736 A | 6/1997 | Jacobs et al. | |
| 5,759,028 A * | 6/1998 | Bozman | 433/9 |
| 5,762,192 A | 6/1998 | Jacobs et al. | |
| 6,089,861 A * | 7/2000 | Kelly et al. | 433/9 |
| 6,213,767 B1 | 4/2001 | Dixon et al. | |
| 6,482,002 B2 | 11/2002 | Jordan et al. | |

* cited by examiner

Primary Examiner—Jacob K. Ackun, Jr.
(74) Attorney, Agent, or Firm—Lloyd L. Zickert

(57) ABSTRACT

Package and method of packaging ready mountable bondable dental appliances wherein the appliances include a body and a base, the base consisting of a cured layer of polymer resin and an uncured layer of polymer resin that may be light-curable or chemically curable. The package includes a compartmented carrier with bondable appliances in the compartments and enclosed in a hermetically sealed bag.

25 Claims, 3 Drawing Sheets

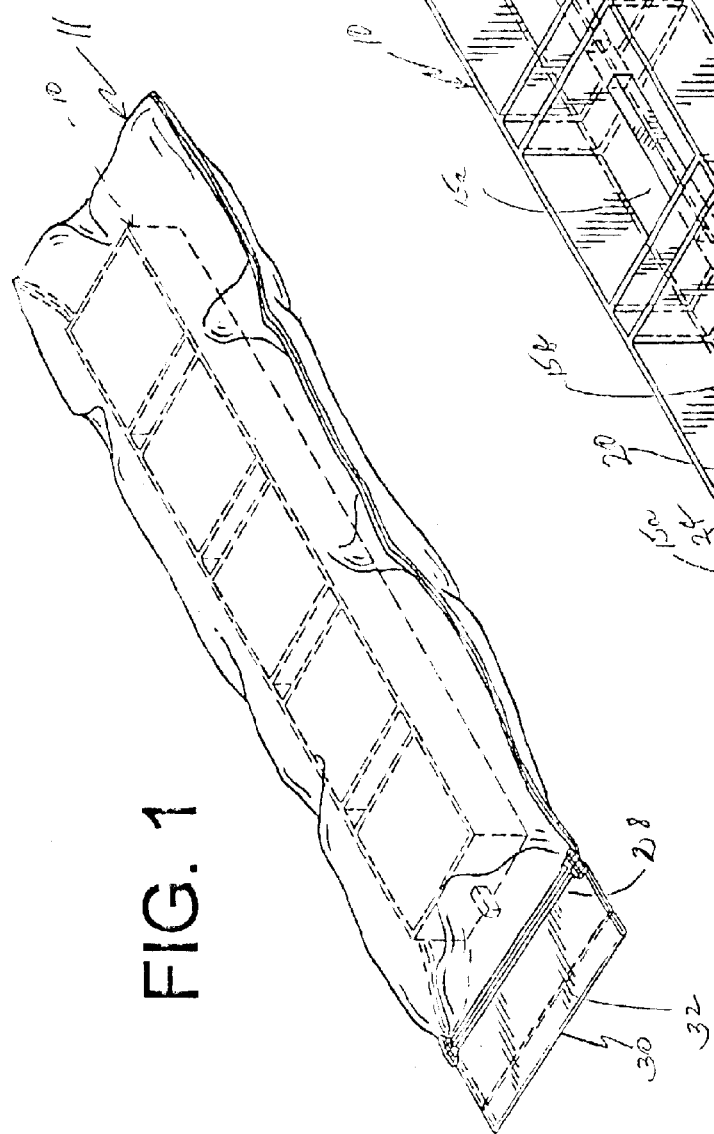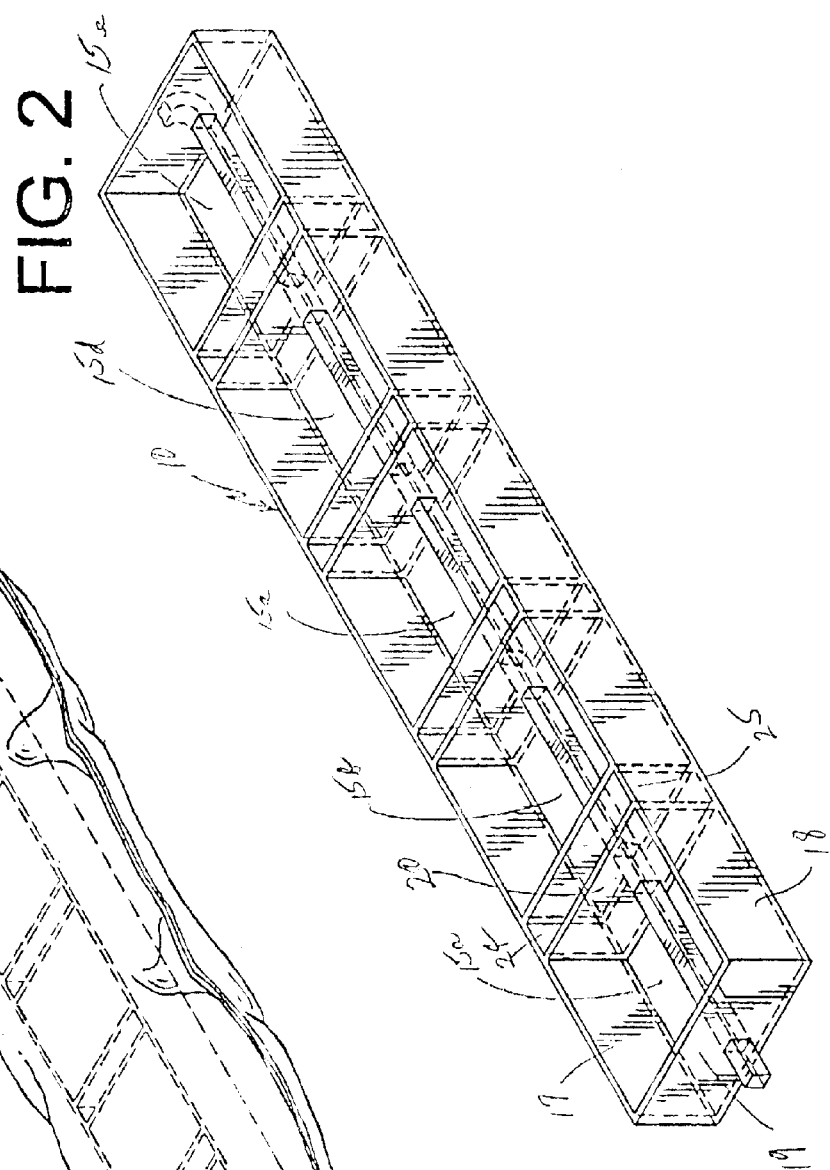

PACKAGE FOR READY MOUNTABLE BONDABLE ORTHODONTIC APPLIANCES AND METHOD OF MAKING SAME

DESCRIPTION

This invention relates in general to a package for a bondable dental appliance ready for mounting, and more particularly to a package for a ready mountable appliance in the form of a carrier having at least one compartment into which the appliance may be inserted and held, and which is enclosed in a hermetically sealed bag for shipment and/or storage.

BACKGROUND OF THE INVENTION

Heretofore, it has been well known to package bondable appliances having an uncured coating of light-curable adhesive paste, as shown in U.S. Pat. Nos. 4,978,007; 5,172,809; 5,328,363; 5,348,154; 5,538,129; 5,636,736; and 5,762,192. The appliances disclosed in these patents include a metallic or ceramic base on which the coating of light-curable adhesive is applied, and are placed in individual pocketed trays for shipping.

It has also been known to provide ready mountable orthodontic appliances having a coating of pressure-sensitive adhesive on their base that is protected during shipment with a releasable backing.

The above prior art packaging systems are not suitable for packaging appliances with a bilayer base of the type disclosed in my copending application Ser. No. 10/285,742, and which is incorporated herein by reference.

SUMMARY OF THE INVENTION

The present invention relates to a package and method of packaging a dental appliance having a bilayer base consisting of a layer of cured polymer resin and a layer of uncured polymer resin of the same family. Preferably, the uncured polymer resin is light-curable, although it may be chemically curable. The uncured light-curable polymer resin may be of any suitable type such as the Python Light Cure Adhesive sold by TP Orthodontics, Inc. of LaPorte, Ind. "Python" is a trademark owned by TP Orthodontics, Inc. Similarly, the chemical cure resin may be of any suitable activator-curable type, such as the Python One Step Adhesive or the Right-On no mix adhesive sold by TP Orthodontics, Inc. "Python One Step" and "Right-On" are trademarks owned by TP Orthodontics, Inc. In this application, reference to a polymer resin is intended to relate to any suitable light or chemically curable adhesive for bonding appliances to hard surfaces, such as teeth.

The package of the invention includes an egg crate type carrier frame of a suitably substantially rigid plastic formed of interconnecting walls and dividers or partitions that define one or more open-ended compartments. Preferably, the carrier will be provided with a plurality of compartments for a plurality of appliances, but it should be appreciated that it could be made in a form to accept a single appliance. The compartments are generally rectangular in configuration, but it should be appreciated that they could be made of ally geometrical shape for receiving a particular appliance of like geometrical shape. For example, some orthodontic lugs or cleats may have a round-shaped base, and in that event the compartments may be a round-shaped cross section. Brackets and tulles normally have a rectangularly shaped base, and therefore rectangularly shaped compartments are particularly suited for such appliances. For purposes of illustrating and describing the invention, the drawings show a carrier with rectangular openings.

The compartments may be of a type having a substantially uniform cross section between their ends or of a tapered cross section. Where the compartments are substantially rectangular in configuration, the appliances with a cured layer of polymer resin are placed in the compartments such that the face of the cured layer will be spaced inwardly from one end of the compartment so that a layer of uncured polymer resin can be applied to the cured layer while the appliance is positioned within a compartment. The uncured layer of adhesive is screeded along the carrier to form the layer substantially flush with the ends of the compartments thereby establishing the thickness of the layer, and other retainer means is provided to assist in retaining the appliance within the compartment. For example, where the appliances are brackets having an archwire slot, a wire may be slidably received in the carrier for mating with the archwire slot to retain the brackets at a predetermined position prior to adding the uncured layer of polymer resin.

Following the application of the uncured layer of resin, the carrier with the appliances is then inserted into a bag and hermetically sealed in the bag. The bag may be of any suitable light opaque material to not only prevent the exposure of a light-curable polymer resin to a wavelength of light energy that would cause curing of the resin. The bag would also prevent the entry of any contaminants, as well as ambient air and/or any water vapor. It is also preferable to flush the interior of the bag, as well as the carrier with the appliances with an inert gas to remove the ambient air prior to hermetically sealing the bag. This procedure will enhance the shelf life of the uncured layer of polymer resin. The bag may be hermetically sealed by any suitable method, and the end of the bag that is sealed may also be provided with a suitable well known reclosable fastener that would allow, after breaking of the hermetic seal, opening of the bag to permit removal and use of some of the appliances from the carrier, and thereafter closing the bag for at least some period of time before use of the unused appliances.

The bag material may be of any suitable polymeric material such as a polyethylene or polyester that would be impermeable to ambient air, water vapor, contaminants, and, where a light-curable resin is used, to also be impermeable to light energy that would cure the resin.

It is therefore an object of the present invention to provide a package for shipment and/or storage of dental appliances having a base including a cured layer of a polymer resin and an uncured layer of a polymer resin to protect the integrity of the uncured layer of resin before usage of the appliances.

Another object of the present invention is to provide a package for bondable dental appliances ready to be mounted on teeth that includes a sufficiently rigid carrier having compartments into which the bondable appliances may be individually positioned and a bag for completely enclosing the carrier and appliances against contamination to prevent the curing of the uncured layer of the polymer resin and to provide a desired shelf life.

A further object of the present invention is to provide a package in the form of a carrier and bag to transport bondable appliances having a cured layer of polymer resin and an uncured layer of polymer resin.

A still further object of the present invention is to provide a method of packaging bondable appliances with a base having a cured layer of polymer resin and an uncured layer of polymer resin.

Another object of the present invention is to provide a package for ready mountable orthodontic appliances having a bilayer base with a layer of cured polymer resin and a layer of light-curable polymer resin which will maintain the appliances separate from each other, and individually readily removable for direct mounting on a tooth.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of a package for bondable appliances according to the present invention and showing in phantom an appliance carrier within the bag;

FIG. 2 is a perspective view of the carrier for the bondable appliances according to the invention;

DESCRIPTION OF THE INVENTION

Figure 3:
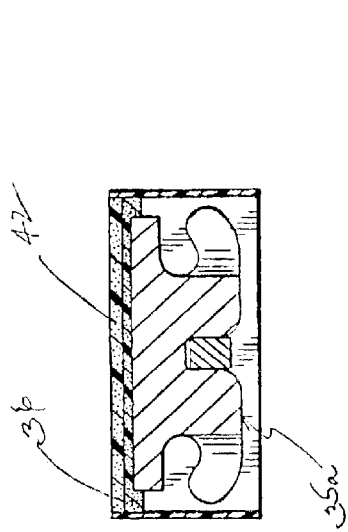
FIG. 3 is a transverse sectional view taken through a carrier and an appliance according to the invention and illustrating that the appliance with its cured layer of polymer material is inserted within a compartment of a carrier for the application thereafter of the uncured layer of polymer resin.

Referring now to the drawings, and particularly to the embodiment illustrated in FIGS. 1 to 4, the package of the invention for ready mountable dental appliances such as orthodontic appliances includes a carrier or frame 10 and a plastic bag 11. The carrier is loaded with appliances having an uncured layer of polymer resin of a suitable type, and then inserted into the bag. The interior of the bag and the carrier with the appliances are flushed with a suitable gas to define an atmosphere for enhancing the life of the uncured resin, and then hermetically sealed for shipment and/or storage.

The carrier include walls and partitions for defining one or more compartments for receiving a bondable appliance with an uncured layer of polymer resin. The embodiment illustrated in FIGS. 1 to 4 illustrates a carrier having five appliance-receiving compartments, each of which would be loaded with an appliance having an uncured layer of resin prior to insertion into a bag that is hermetically sealed. More specifically, the carrier 10 is in the form of an egg crate frame where the compartments are open at the top and bottom ends. The compartments or openings in the carrier are designated 15a, 15b, 15c, 15d and 15e. Each is defined by opposed walls 17 and 18 and end wall 19 and an opposing wall or partition 20. While the compartments are rectangular in cross section, they may be of whatever suitable geometric shape commensurate with the appliance to be packaged.

The carrier is preferably injection molded of a suitable plastic such as a polymeric material, such as a polyester or polyethylene plastic, and each of the compartments is connected together by spacing walls 24 and 25 in order to provide a reinforced carrier having a sufficient stiffness to support individual appliances and maintain the integrity of the carrier during handling. It should also be appreciated that the carrier may be made of a suitable paperboard if desired, and further that the walls and partitions are relatively thin. Following use of the carrier after removal of the appliances, it may be suitably discarded.

The bag 11 for use in receiving the carrier 10 is in a sleeve form and initially open at one end. Following insertion of the carrier with the appliances into the bag, the bag may be flushed with nitrous oxide or some other suitable gas in order to render the atmosphere within the bag essentially inert in order to enhance the life of the uncured layer of polymer resin. At the mouth end of the bag a reclosable fastener 28 is optionally provided for the purpose of permitting the user to reclose the bag after it is opened and where some of the appliances are removed from the carrier so that the remaining appliances can be preserved for later use in an airtight atmosphere. Where the uncured resin is light-curable, the bag will be of a material to prevent the transmission of the curing light energy.

Additionally, the end of the mouth of the bag includes a seal 30 in order to completely hermetically seal the bag. This seal may be formed by heat, adhesive, or otherwise. It will be appreciated that the bag will be made of a suitable plastic film such a polyethylene that would be flexible and easy to handle for receiving the carrier of appliances.

Also at the mouth end of the bag a weakened tear-off line 32 is provided to facilitate tearing off the seal 30 prior to opening the mouth of the bag and the reclosable fastener in order to obtain access so that the carrier with the appliances may be removed.

Figure 4:
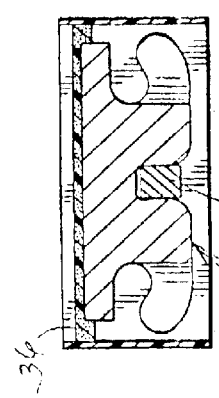
FIG. 4 is a view similar to FIG. 3 with the exception that it additionally shows the layer of uncured polymer resin on the layer of uncured resin.
Figure 5:
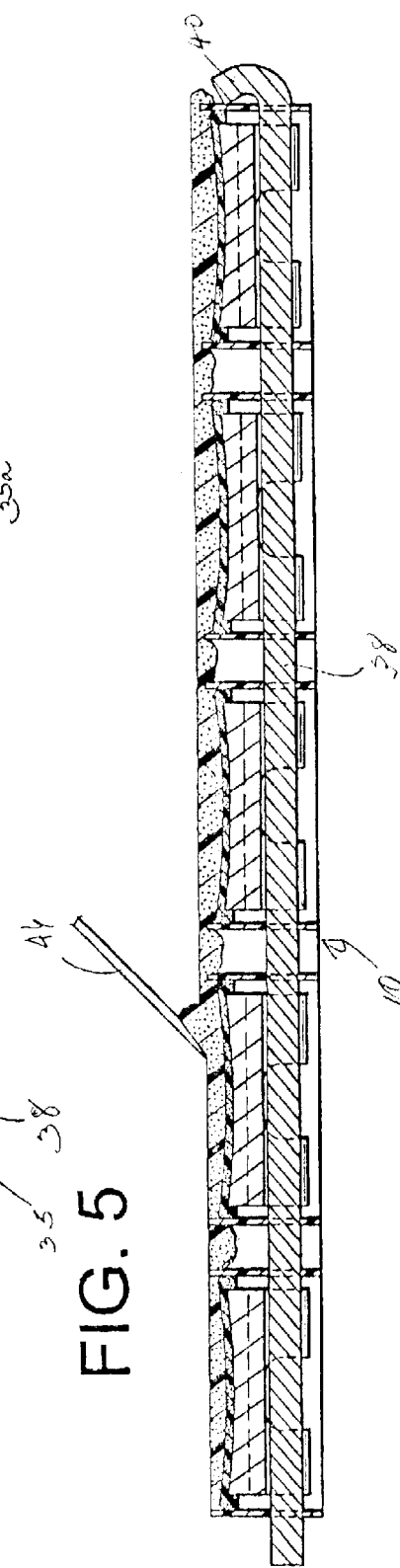
FIG. 5 is a longitudinal and sectional view of the carrier of the invention and illustrating the manner in which the uncured layer of polymer resin is screeded along the carrier so that it will be flush with the upper ends of the compartments of the carrier, and a removable retention wire for retaining the appliances in the carrier at a predetermined position during application of the uncured layer and during shipment.

In order to illustrate the method of packaging dental appliances, reference is made to FIGS. 3, 4 and 5, which illustrate the loading of the compartments with orthodontic brackets 35 having a cured layer of polymer resin 36 on the mounting side of the bracket. In order to properly position the bracket in the compartments, a retention wire 38 is mounted on the carrier 10 for engagement by the archwire slots of the brackets and limiting the inserted position of the appliance relative to the compartment opening for application of the uncured layer of adhesive; and for retention within the compartment. Each of the brackets includes an archwire slot on the outer face opposite the bonding side for receiving an archwire during treatment of a patient. The retention wire 38 is rectangular in cross section, although it could be round or of any other configuration that would be receivable in the archwire slots of the brackets. It will be appreciated where the carrier is used to be loaded with molar tubes or other bondable appliances, the retention wire would be formed to properly position the appliances in the compartments for later receipt of the uncured layer of polymer resin. In this embodiment, the retention wire, as shown in FIG. 5, extends through openings provided in the walls and partitions and may thereafter be slidably positioned relative to the carrier to release the appliances through the bottom of the carrier.

One end of the retention wire is shown with a band 40 that prevents the wire from sliding through the carrier except in one direction. It will be appreciated that the other end of the wire may also be bent to lock the wire in place if so desired after the carrier is loaded with bondable appliances. Thereafter, removal of the retention wire may easily be accomplished by unbending an end so that the retention wire may be slid partially or completely out of the carrier in one direction.

FIG. 4 shows an appliance 35*a* that not only includes the cured layer 36 of a suitable polymer resin but also an applied uncured layer 42.

The thickness of the uncured layer of polymer resin is not only determined by the predetermined positioning of the appliances within the compartments prior to the application of the resin but also by the screediing of excess uncured resin, such as shown by use of the screed 46 in FIG. 5. Following the application of the uncured layer of polymer resin to load the space provided between the face of the cured layer of resin and the ends of the walls and partitions of the carrier, the excess uncured resin is screeded to define the thickness of the uncured layer of resin. The screed 46 would have a width greater than the width of the carrier and be drawn along the ends of the walls and partitions to remove the excess resin so that the outer face of the uncured resin would be flush with the ends of the walls and partitions of the carrier, as shown in FIG. 4, and also at the left-hand end of FIG. 5. Once the excess resin is screeded front the carrier, the carrier with the appliances can then be inserted into the enclosing bag 11, and further processed for hermetically sealing the carrier and appliances within the bag.

In addition to the retention of the brackets 35 in the compartments of the carrier by the retention wire 38, it will be appreciated that the polymer resin will have a tackiness to also hold the appliances in place by contact between the uncured layer of resin and the walls and partitions of the compartment at the upper end. Thus, the appliances are not only retained in place in the compartments with the retention wire 38 but also by the uncured layer of polymer resin. It will be appreciated that the viscosity of the uncured resin will be such as to stay put on the appliances and within the compartments during any reasonable handling.

It will be appreciated that the polymer resin may be of any suitable type as previously mentioned but preferably the uncured layer of polymer resin will be of the same family as the cured polymer resin. For example, if the cured layer of polymer resin is light-curable, then the uncured layer would also be light-curable. Similarly, if the cured layer of resin is chemically curable, then the uncured layer of resin would be of a chemically curable type which would require the use of an activator applied to the exposed face of the uncured layer of resin or to the tooth on which the appliance is to be mounted when it is desired that the layer be cured for adhering to a tooth. Otherwise, if the resin is light-curable, a suitable light source would be used for curing the uncured layer once it is mounted and properly positioned onto a tooth.

Figure 6:
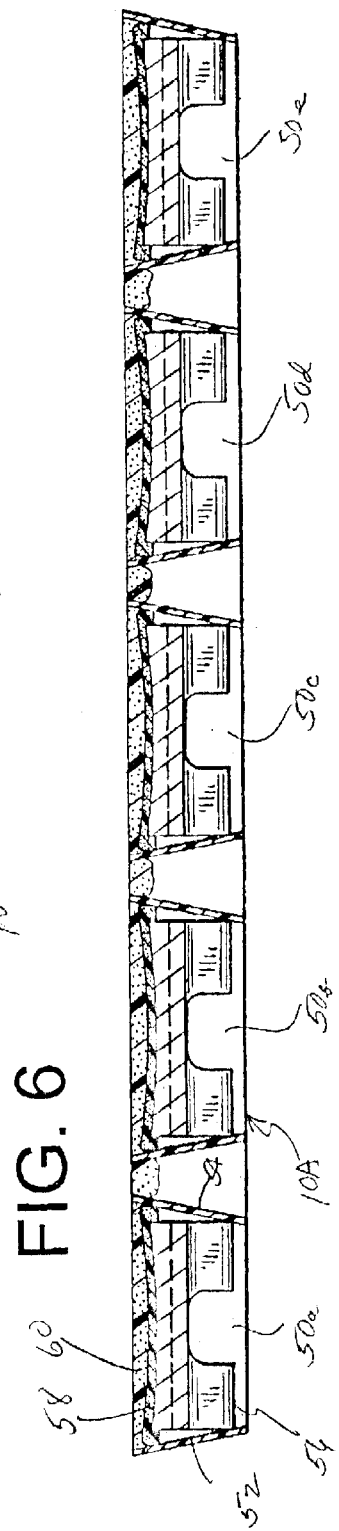
FIG. 6 is a view similar to FIG. 5 with the exception that it shows a modified carrier with the uncured layer of adhesive having been screeded and further that the cross-sectional shape of the compartments are tapered to assist in the retention of the appliances within the compartments and to eliminate the need for a retention wire as shown in FIG. 5.

Referring now to the embodiment of FIG. 6, another form of retention of the appliances in the compartments is shown wherein the carrier, generally designated by the numeral 10A, includes compartments that have tapered walls with the opening at the lower end being smaller than the overall configuration of the appliance. The carrier 10A includes a plurality of compartments and in this embodiment five compartments 50*a*, 50*b*, 50*c*, 50*d*, and 50*e*. Each of the compartments includes opposed walls 52 and 54 that are tapered such that the bracket engages the walls near the lower end openings of the compartments. Thus, it is not necessary to include a retention wire to retain the appliances in the compartments. Otherwise, the appliances 56, like the appliances in the embodiment of FIGS. 3 to 5, include a cured layer of polymer resin 58 and an uncured layer of polymer resin 60. When removing the appliances from the compartments, they may be removed by pushing them upwardly through the upper opening ends of the compartments or by bending the carrier to render the walls substantially parallel so that the bracket may be discharged from the lower ends of the openings.

Figure 7:
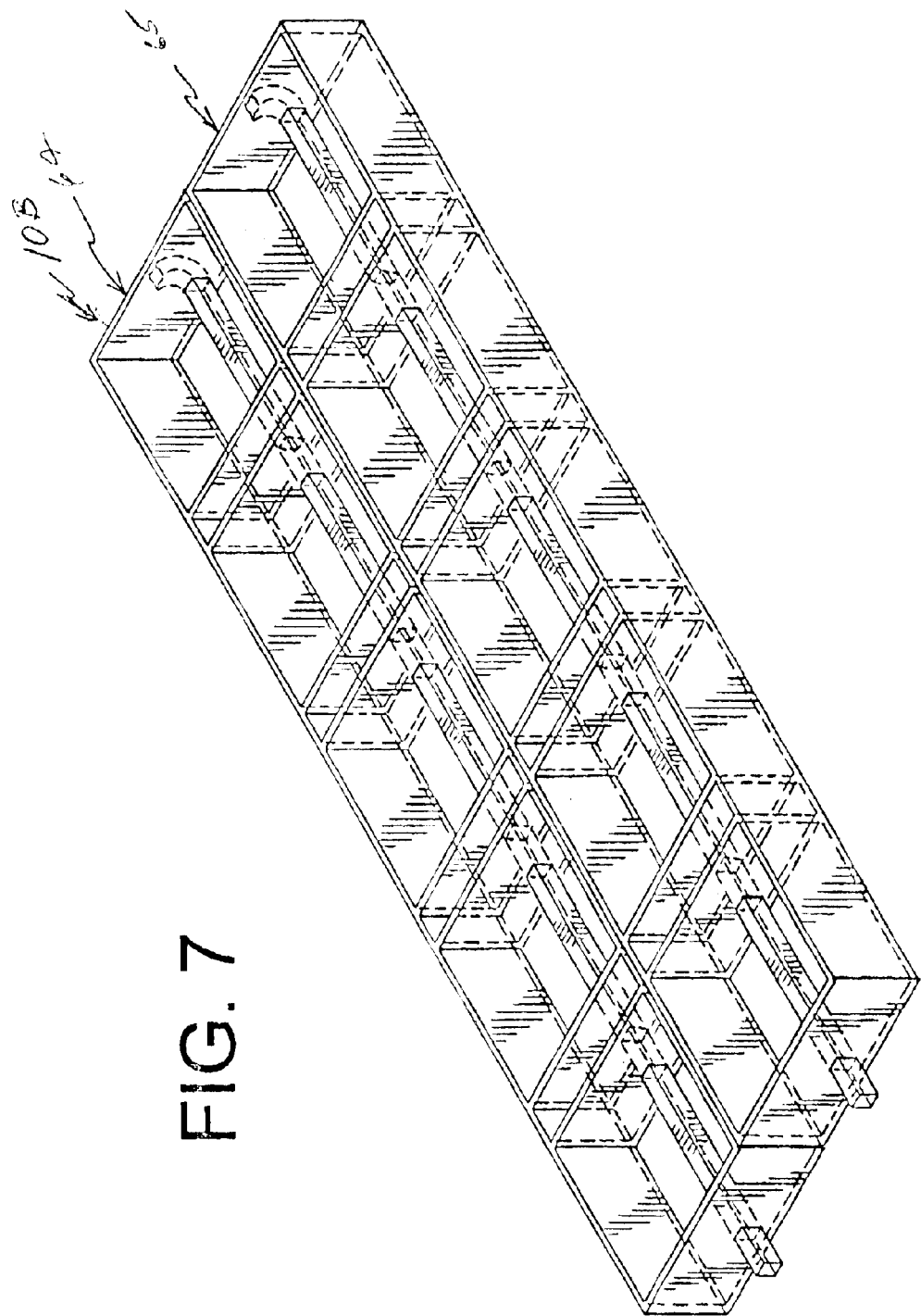
FIG. 7 is a perspective view of a modification of the invention wherein side-by-side rows of compartments are formed in a carrier.

As above described, the carrier may be formed to have any number of compartments for receiving a ready mountable dental appliance. For example, as shown in FIG. 7, a carrier, generally designated by the numeral 10B, includes a double row of compartments by joining together adjacent frames 64 and 65. This carrier would therefore be suitable for being loaded with ten appliances that are ready for mounting on teeth. The bag for this carrier would be sized to receive the carrier and therefore be of a different size than that shown in the embodiment of FIG. 1. Otherwise, the operation of this carrier would be like the carrier 10. Further, after each of the compartments is loaded with an appliance and the application of uncurable resin is made, the excess resin would be screeded to limit the thickness of the uncured layer of resin and render it flush with the upper ends of the walls and partitions of the compartments in a similar manner as shown in FIG. 5.

In view of the foregoing, it will be appreciated that the invention is to a package for ready mountable bondable dental appliances, and a method of making the package wherein a carrier is provided with compartments to be loaded with appliances having an uncured layer of resin and then enclosed in a hermetically sealed bag for shipment and/or storage. When the user receives the package of appliances, all of the appliances could be used at one time for a patient or any number can be used and the bag could be reclosed so that the remaining appliances could be used at a later time.

Other objects, features and advantages of the invention will be apparent from the following detailed disclosure, taken in conjunction with the accompanying sheets of drawings, wherein like reference numerals refer to like parts.

What is claimed is:

1. A packaged dental appliance comprising a carrier having a plurality of compartments open at each end, a ready mountable bondable dental appliance in each of said compartments, each appliance having a base with a layer of cured polymer resin and a layer of uncured polymer resin, and a hermetically sealed bag of flexible plastic in which the carrier and appliances are received.

2. Te package of claim 1, wherein the layer of uncured polymer resin is light-curable, and the sealed bag of flexible plastic is opaque to be light energy that would cure the uncured resin.

3. The package of claim 1, wherein the layer of uncured polymer resin is chemically curable.

4. The package of claim 1, wherein the resins are of the same family.

5. The packaged dental appliance of claim 1, wherein the dental appliance is a dental element intended for attachment to a tooth.

6. The packaged dental appliance of claim 5, wherein the dental element is from the group consisting of orthodontic brackets, tubes, lugs, hooks, cleats, buttons and retainers, and restoratives.

7. The packaged dental appliance of claim 1, wherein said bag is flushed with a gas before being hermetically sealed.

8. The packaged dental appliance of claim 1, wherein said bag includes a reclosable fastener.

9. The packaged dental appliance of claim 2, wherein said bag material blocks the transmission of light energy capable of curing said uncured layer of polymer resin.

10. The packaged dental appliance of claim 1, which further includes means for releasably retaining the appliances in the compartments.

11. The packaged dental appliance of claim 1, wherein the appliances are orthodontic brackets having an archwire slot, and a slidable wire retainer extends through the carrier in engagement with the archwire slots of each bracket to retain the brackets in the carrier.

12. The packaged dental appliance of claim 1, wherein each compartment has a substantially uniform cross-section from end to end.

13. The packaged dental appliance of claim 1, wherein the compartments have a tapered cross-section to retain the appliances in the compartments.

14. A packaged bondable orthodontic bracket comprising:
a bracket having a body and a base, the base including a layer of cured polymer resin, and a layer of uncured light-curable polymer resin, the bracket being ready for mounting on a tooth, and a carrier having at least one compartment open at the top and bottom thereof, said compartment receiving said bracket, means retaining the bracket in the compartment, and a bag of substantially opaque material enclosing the carrier and bracket, wherein the interior of the bag and the carrier with the bracket are flushed with nitrous oxide and hermetically sealed.

15. A package for at least one bondable orthodontic appliance having a body and a base on one side for mounting the appliance on a tooth, said base including a layer of cured adhesive on the body and a layer of uncured adhesive over the cured layer, said package comprising a box-shaped frame, said frame including a plurality of interconnected walls and partitions defining at least one compartment open at both ends and sized to receive said appliance such that the uncured layer is substantially flush with one end of the walls and partitions, and means for releasably retaining said appliance in a compartment, and a hermetically sealed bag of opaque material receiving said frame and appliance.

16. The package of claim 15, wherein the appliance is from the group consisting of brackets, tubes, lugs, cleats, hooks, buttons, and retainers.

17. The package of claim 15, wherein said bag includes a reclosable fastener.

18. The package of claim 15, wherein said retaining means includes a wire slidable through the walls or partitions for engaging the appliance body.

19. The package of claim 15, wherein the cross section of the compartment is substantially uniform from end to end.

20. The package of claim 15, wherein the retaining means is defined by a uniformly tapered cross section in the compartment.

21. A method of packaging ready mountable bondable dental appliances for storage and/or shipment, wherein the appliances include a body and a base, the base including a layer of cured polymer resin and a layer of uncured polymer resin, the steps comprising:
providing a carrier for the appliances, wherein the carrier includes a plurality of compartments open at both ends,
inserting appliances with a cured layer of polymer resin within said compartments such that the face of the cured layer is spaced from an end of the compartments,
applying an uncured layer of polymer resin over the cured layers acil flush with the ends of the compartments,
inserting the carrier and appliances into the open end of a plastic bag of impermeable material, and
forming a hermetic seal at the open end of the bag.

22. The method of claim 21, which further comprises the step of providing an airtight reclosable fastener to reclose the bag once the hermetic seal is broken.

23. The method of claim 22, which further comprises the step of flushing the bag, carrier, and appliances with nitrous oxide before forming the hermetic seal.

24. The method of claim 22, wherein the layer of uncured polymer resin is light-curable.

25. The method of claim 22, wherein the layer of uncured polymer resin is chemically curable.

* * * * *